United States Patent [19]

Washburn et al.

[11] Patent Number: 4,672,029
[45] Date of Patent: Jun. 9, 1987

[54] COLOR-FORMING COUPLERS AND THEIR USE IN THE ANALYTICAL DETERMINATION OF HYDROGEN PEROXIDE OR OTHER ANALYTES

[75] Inventors: William N. Washburn, Ionia; Ewell R. Cook, Rochester; Glen M. Dappen, Webster, all of N.Y.

[73] Assignee: Eastman Kodak Company, Rochester, N.Y.

[21] Appl. No.: 678,931

[22] Filed: Dec. 6, 1984

[51] Int. Cl.$^4$ .......................... C12Q 1/62; C12Q 1/54; C12Q 1/28; G01N 33/72
[52] U.S. Cl. ........................................ 435/10; 435/14; 435/28; 435/805; 435/810; 546/23; 436/66
[58] Field of Search ...................... 435/28, 14, 25, 10, 435/805, 810; 546/23, 171, 172, 178, 152; 548/413, 482, 491; 436/66, 904

[56] References Cited

U.S. PATENT DOCUMENTS

| | | | |
|---|---|---|---|
| 3,184,466 | 5/1965 | Hennig et al. | 548/491 X |
| 3,630,847 | 12/1971 | Rey et al. | 435/14 |
| 3,887,620 | 6/1975 | Glamkowski et al. | 564/15 |
| 4,042,335 | 8/1977 | Clément | 435/14 X |
| 4,247,631 | 1/1981 | Nix et al. | 435/10 |
| 4,251,629 | 2/1981 | Yamanisi et al. | 435/28 |
| 4,260,679 | 4/1981 | Tsuda et al. | 435/10 |
| 4,265,812 | 5/1981 | Weaver et al. | 534/768 |
| 4,282,144 | 8/1981 | Weaver et al. | 534/768 |
| 4,391,906 | 7/1983 | Bauer | 435/14 |
| 4,396,714 | 8/1983 | Maeda et al. | 435/28 |
| 4,416,982 | 11/1983 | Tsuda et al. | 435/11 |
| 4,418,037 | 11/1983 | Katsuyama et al. | 422/56 |
| 4,452,887 | 6/1984 | Kitajima et al. | 435/14 |
| 4,499,272 | 2/1985 | Hyatt et al. | 546/172 |

FOREIGN PATENT DOCUMENTS

| | | |
|---|---|---|
| 68356 | 1/1983 | European Pat. Off. |
| 71730 | 2/1983 | European Pat. Off. |
| 321007 | 9/1934 | Italy |
| 52-77019 | 6/1977 | Japan |
| 56-37557 | 4/1981 | Japan |
| 56-55199 | 5/1981 | Japan |
| 56-61999 | 5/1981 | Japan |
| 57-79899 | 5/1982 | Japan |
| 57-206399 | 12/1982 | Japan |
| 2095401 | 9/1982 | United Kingdom |

Primary Examiner—Robert J. Warden
Assistant Examiner—Randall E. Deck
Attorney, Agent, or Firm—J. Lanny Tucker

[57] ABSTRACT

Particular heterocyclic compounds are useful as color-forming couplers in analytical compositions, elements and methods. These compounds are represented by the structure:

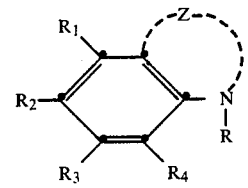

wherein R is a solubilizing group, $R_1$, $R_2$, $R_3$ and $R_4$ are independently hydrogen, alkyl, alkoxy, aryl, aryloxy, a heterocyclic group, halo, amino or R, and Z represents the carbon atoms necessary to complete the nucleus of a 5- or 6-membered fused ring. The color-forming coupler is combined with an oxidizable color developing compound, e.g. 4-aminoantipyrine to provide a chromogenic composition. This composition can be used in solution or dry assays of biological fluids to produce a color dye in the presence of hydrogen peroxide or other analytes, e.g. glucose or uric acid, which react to produce hydrogen peroxide.

23 Claims, No Drawings

COLOR-FORMING COUPLERS AND THEIR USE IN THE ANALYTICAL DETERMINATION OF HYDROGEN PEROXIDE OR OTHER ANALYTES

FIELD OF THE INVENTION

This invention relates to novel compounds, chromogenic composition, elements and methods useful to detect hydrogen peroxide or analytes which react to produce hydrogen peroxide. This invention is particularly useful in clinical chemistry, i.e. in the assay of biological fluids.

BACKGROUND OF THE INVENTION

The detection and quantitative determination of hydrogen peroxide and compounds yielding hydrogen peroxide as a result of chemical or enzymatic reactions are of importance in many areas. For example, they are important in the detection of hydrogen peroxide produced in the enzymatic assay of chemical or biological substances (sometimes called analytes) such as glucose, cholesterol, uric acid, lipase, triglycerides, creatine kinase, etc. in the presence of oxygen. The quantity of analyte present in a test sample is determinable from the amount of hydrogen peroxide produced and detected.

Known compositions for detecting or quantifying hydrogen peroxide in such assays generally comprise a substance having peroxidative activity, e.g. peroxidase, and a material which undergoes a detectable change (e.g. oxidation to a color dye) in the presence of hydrogen peroxide and the peroxidative substance. Various materials which undergo such a detectable change include monoamines, diamines, phenols, leuco dyes and other known dyes or dye formers.

Hydrogen peroxide detection has also been accomplished by the reaction of a color-forming coupler and an oxidizable color developing compound, e.g. 4-aminoantipyrine in the presence of peroxidase. Color-forming couplers which have been used for this purpose include N-substituted anilines, such as those described in U.S. Pat. No. 4,251,629 (issued Feb. 17, 1981 to Yamanisi et al), U.S. Pat. No. 4,260,679 (issued Apr. 7, 1981 to Tsuda et al) and U.S. Pat. No. 4,396,714 (issued Aug. 2, 1983 to Maeda et al). Some of the anilines described in these references have solubilizing groups, e.g. hydroxy or sulfo groups, attached to the nitrogen atom.

Although the dye-providing materials of the prior art are, in general, useful as indicators for hydrogen peroxide determination, there are instances when the concentration of hydrogen peroxide to be analyzed is too low to produce sufficient detectable color from such indicators. In some instances, this shortcoming can be overcome by using increased amounts of dye-providing materials. However, where the analyte concentration is initially low, or where high dilution of the test sample is required, such materials may still provide insufficient detectable color in such instances.

Such a problem of low analyte concentration is particularly acute when analyte determination is attempted with a dry analytical element, e.g. with the commercially successful elements described in U.S. Pat. No. 3,992,158 (issued Nov. 16, 1976 to Przybylowicz et al). In such instances, the indicator or reagent layer present in such elements is very thin, and the dye-providing material concentration is necessarily low. Hence, the density of the color formed from low level analytes, or even from abnormally low concentrations of high level analytes, can be rather low. However, it would be desirable to use such elements to assay for analytes present at low concentrations.

Hence, there is a continuing need in the art for a means to detect low concentrations of either hydrogen peroxide or analytes which react to produce hydrogen peroxide.

SUMMARY OF THE INVENTION

The present invention utilizes a particular class of N-substituted heterocyclic color-forming couplers to overcome the deficiencies of known color-forming couplers. The couplers described herein can be advantageously used to detect low concentrations (e.g. less than about 0.3 millimolar) of hydrogen peroxides or analytes which react to produce hydrogen peroxide in both solution and dry assays. These color-forming couplers are particularly useful for the determination of hydrogen peroxide generated by one or more (i.e. coupled or uncoupled) enzymatic reactions in response to an analyte such as glucose, galactose, amino acids, uric acid, lipase, triglycerides, cholesterol, creatine kinase, and the like.

Therefore, in accordance with this invention, a chromogenic composition for the determination of hydrogen peroxide in an aqueous liquid comprises:
a color-forming coupler of the structure

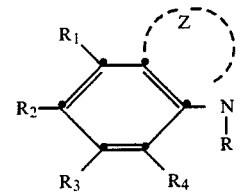

wherein
R is a solubilizing group,
$R_1$, $R_2$, $R_3$ and $R_4$ are independently hydrogen, alkyl, alkoxy, aryl, aryloxy, a heterocyclic group, halo, amino or R, and
Z represents the carbon atoms necessary to complete the nucleus of a 5- or 6-membered fused ring, and
an oxidizable color developing compound which is capable of reacting with the coupler in the presence of hydrogen peroxide and a substance having peroxidative activity to produce a color dye.

This invention also provides a dry analytical element for the determination of hydrogen peroxide or an analyte which reacts to produce hydrogen peroxide in an aqueous liquid. Such an element comprises an absorbent carrier material and the chromogenic composition described above. In preferred embodiments of the invention, the element includes a support having thereon a porous spreading zone.

This invention further provides a method for determining hydrogen peroxide or an analyte which reacts to produce hydrogen peroxide in an aqueous liquid. This method comprises the steps of: in the presence of a compound having peroxidative activity, physically contacting a sample of the liquid with the chromogenic composition described above to produce a color dye, and detecting that dye.

Novel color-forming coupling compounds of this invention are represented by the structure:

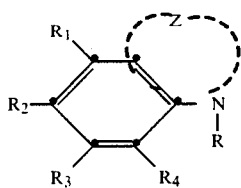

wherein R has one or more phosphono groups or equivalent esters or salts, $R_1$, $R_2$, $R_3$ and $R_4$ are independently hydrogen, alkyl, alkoxy, aryl, aryloxy, a heterocyclic group, halo, amino or R, and Z represents the carbon atoms necessary to complete the nucleus of a 5- or 6- membered fused ring.

DETAILED DESCRIPTION OF THE INVENTION

The color-forming coupling compounds useful in the practice of this invention are N-substituted quinoline or indole compounds (or saturated counterparts) which have at least one solubilizing group attached to the nitrogen atom of the quinoline or indole ring. The compounds can otherwise have one or more other substituents as long as the dye-forming capability of the compound is not impaired.

In particular, the useful heterocyclic compounds can be represented by the structure:

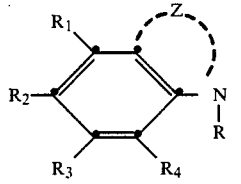

wherein R is a solubilizing group, e.g. a monovalent group containing one or more sulfo, hydroxy, carboxy, phosphono, quaternary amino, sulfonium, phosphonium and like charged moieties, or equivalent esters or salts (e.g. alkali metal salts). For example, R can be alkyl, preferably of 1 to 6 carbon atoms (e.g. methyl, ethyl, propyl, isopropyl, butyl, pentyl, etc.); cycloalkyl, preferably of 5 to 10 carbon atoms (e.g. cyclopentyl, cyclohexyl, etc.), or aryl, preferably of 6 to 10 carbon atoms in the nucleus (e.g. phenyl, p-methylphenyl, naphthyl, etc.), each of which contains one or more of the described solubilizing groups. The groups defined for R can have one or more other non-solubilizing substituents (e.g. alkoxy, halo, amino, nitro, etc.), if desired, and can contain additional groups linked together by oxy, thio, carbonyl, carbonamido, sulfonamido or other linking groups known in the art. The R groups impart water solubility to the color-forming coupler so that it is easily used in the assays described below.

Preferably, R is alkyl substituted with one or more sulfo, hydroxy, carboxy or phosphono moieties or equivalent esters or salts. More preferably, R is —$(CH_2)_m SO_3 M$ or —$(CH_2)_m PO(OR_5)(OR_6)$ wherein m is 1 to 5, M is a suitable cation (e.g. hydrogen, alkali metal, ammonium, etc.), and $R_5$ and $R_6$ are independently hydrogen or alkyl of 1 to 5 carbon atoms (e.g. methyl, ethyl, isopropyl, etc.). Most preferably, R is —$(CH_2)_m SO_3 M$ wherein m is 1 to 5. One or more hydrogen atoms of the alkylene chains in these preferred R groups can be replaced with other solubilizing or non-solubilizing groups, as described in the preceding paragraph.

In the structure illustrated above, $R_1$, $R_2$, $R_3$ and $R_4$ are independently hydrogen, substituted or unsubstituted alkyl, preferably of 1 to 10 carbon atoms, (e.g. methyl, ethyl, isopropyl, chloromethyl, 2-hydroxyethyl, methoxymethyl, benzyl, etc.), substituted or unsubstituted alkoxy, preferably of 1 to 10 carbon atoms (e.g. methoxy, ethoxy, benzyloxy, etc.), substituted or unsubstituted aryl, preferably of 6 to 10 carbon atoms in the nucleus (e.g. phenyl, xylyl, p-methoxyphenyl, naphthyl, m-sulfophenyl, etc.), substituted or unsubstituted aryloxy, preferably of 6 to 10 carbon atoms in the nucleus (e.g. phenoxy, etc.), a substituted or unsubstituted heterocyclic group, preferably having 5 to 10 carbon and heteroatoms (sulfur, oxygen, nitrogen, etc.) in the nucleus (e.g. pyridyl, triazinyl, furyl, thienyl, etc.), halo (e.g. fluoro, chloro, bromo, etc.), amino (primary, secondary or tertiary), or an R group as defined above.

Preferably, $R_1$, $R_2$, $R_3$, and $R_4$ are independently hydrogen, substituted or unsubstituted alkyl or 1 to 3 carbon atoms, substituted or unsubstituted alkoxy of 1 to 3 carbon atoms or halo. More preferably, at least two of the groups are hydrogen, such as $R_2$ and $R_4$. Most preferably, each of $R_1$, $R_2$, $R_3$ and $R_4$ is hydrogen.

Z represents the carbon atoms necessary to complete the nucleus of a N-substituted 5- or 6-membered fused ring (e.g. forming an indole, quinoline, dihydroindole, tetrahydroquinoline ring). This fused portion of the ring can be saturated or contain one unsaturated carbon to carbon double bond. It can have one or more substituents including, but not limited to, the groups defined for $R_1$, $R_2$, $R_3$ and $R_4$ above. Preferably, Z completes a saturated portion of the ring. More preferably, it represents the carbon atoms necessary to complete the nucleus of a saturated 6-membered fused ring (i.e. forming an N-substituted tetrahydroquinoline). Preferred fused ring substituents include halo and substituted or unsubstituted alkyl of 1 to 3 carbon atoms. Most preferably, the fused ring is saturated and unsubstituted.

In certain embodiments, novel color-forming couplers of this invention are represented by the structure shown above wherein R is defined as having one or more phosphono groups or equivalent esters or salts. Preferably, in such embodiments, R is —$(CH_2)_m PO(OR_5)(OR_6)$ wherein m is 1 to 5, and $R_5$ and $R_6$ are independently hydrogen or alkyl of 1 to 5 carbon atoms as defined above. More preferably, $R_1$, $R_2$, $R_3$ and $R_4$ in the illustrated structure are independently hydrogen, substituted or unsubstituted alkyl of 1 to 3 carbon atoms, substituted or unsubstituted alkoxy of 1 to 3 carbon atoms or halo, and Z represents the carbon atoms necessary to complete the nucleus of a N-substituted 6-membered fused ring as described above. Preferably, this fused ring portion is saturated. One or more of the hydrogen atoms of the alkylene chain of the R group can be replaced with a solubilizing or non-solubilizing group as described for R in general above.

Examples of color-forming couplers useful in the chromogenic compositions of this invention include the following. The compounds identified with * are preferred. The last three listed compounds are representative novel phosphono-containing color-forming couplers. The $\lambda_{max}$ of the color dye formed by reaction of the color-forming coupler with 4-aminoantipyrine is also given.

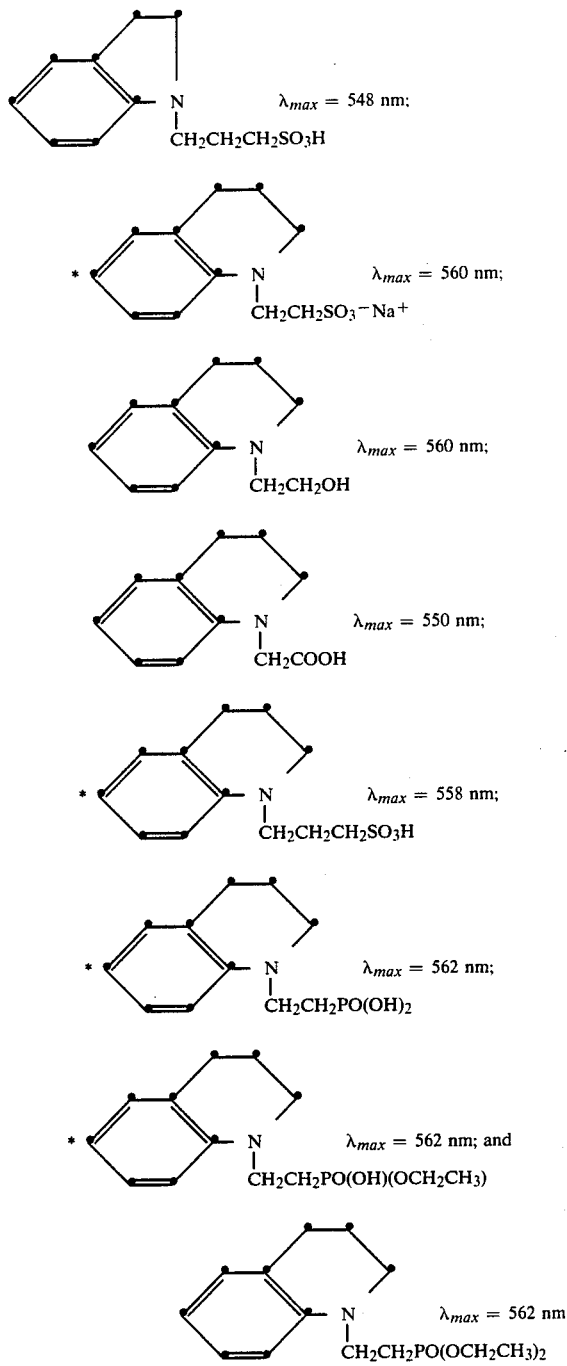

In the presence of hydrogen peroxide and a compound having perioxidative activity (defined hereinbelow), the described color-forming coupler reacts with an oxidizable color developing compound to produce a color dye. Any of a number of such color developing compounds can be used in this invention, including but not limited to 2-aminoantipyrine, 4-aminoantipyrine, 2-thiophenecarboxylic acid hydrozide, benzidine and its homologs, 3-methyl-2-benzthialinone hydrazone, p-phenylenediamines and p-aminophenols. A preferred oxidizable color developing compound is 4-aminoantipyrine.

The color dye-forming reaction can be illustrated by the following representative reaction:

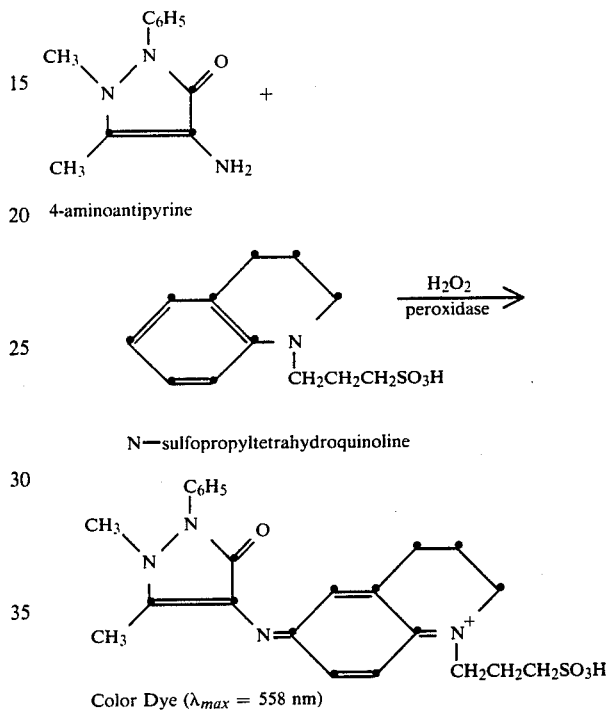

The color-forming couplers useful in this invention can be prepared by any of a number of synthetic methods. In general, they can be prepared by reacting a reduced quinoline or indole with an alkylating agent which contains the R moiety. This agent reacts with the nitrogen atom of the heterocyclic ring, replacing a hydrogen atom on the nitrogen.

For couplers containing an N-sulfoalkyl substituent, the compound is preferably prepared by reacting a reduced quinoline or indole with a sultone in a suitable solvent or with an appropriate halogenated alcohol which is subsequent converted to an N-sulfoalkyl substituent. Specific details of the preparation of preferred color-forming couplers are given below. Other useful preparatory methods are generally described in U.S. Pat. No. 4,282,144 (issued Aug. 4, 1981 to Weaver et al) and in references mentioned therein.

The novel color-forming couplers of this invention having N-phosphono substituents are generally prepared by reacting a reduced quinoline or indole with a brominated phosphonate compound in a suitable solvent. Specific details of the preparation of useful N-phosphono color-forming couplers are given below in Examples 1 and 2.

The chromogenic composition of this invention can be used in both solution and dry element assays. It can optionally comprise a substance having peroxidative activity or a buffer which maintains the pH of the composition in an aqueous environment at from about 4 to about 11.

Substances having peroxidative activity useful in the practice of this invention are also known as peroxidative substances and are capable of catalyzing the oxidation of another substance by means of hydrogen peroxide or another peroxide. Such substances include natural and synthetic peroxidases, cytochromes, hemin, forms of hemoglobin, alkaline hematin, iron sulfocyanate, iron tannate, tungstic acid and its salts, molybdic acid and its salts, chromic salts and the like. Peroxidase is a particularly useful peroxidative substance. A catalytic amount of the peroxidative substance can be used, as is known in the art.

Substantially any buffer can be used in the composition of this invention which maintains the composition at a pH which is conducive to dye formation as well as to the reactions required for a given assay. Generally, the pH is maintained within the range of from about 4 to about 11, but a specific pH will depend on the particular analyte being assayed and the reagents used therein. For example, when a fluid is assayed for uric acid using uricase, the composition pH is generally maintained between about 8 and about 9. When a fluid is assayed for glucose using glucose oxidase, the composition pH is generally maintained between about 4 and about 7. Useful buffers for various assays include carbonates, borates, phosphates, malates, maleates, glutarates, the tris materials, e.g. tris(hydroxymethyl)aminomethane, and others known in the art.

The chromogenic compositions of this invention can be prepared for use in a solution assay by mixing the color-forming coupler with the oxidizable color developing compound. Additional materials can be mixed in as well. The details of preparing and using representative chromogenic compositions are given in Examples 3 and 4 below.

When the chromogenic compositions of this invention are used in solution assays, generally the color-forming coupler is present in a concentration of up to about $10^{-3}$ molar, and preferably from about $5 \times 10^{-5}$ to about $5 \times 10^{-4}$ molar. The oxidizable color developing compound is present in an amount sufficient to react with the coupler. For example, it is generally present in an amount up to 10 millimolar, and preferably from about 0.5 to about 2 millimolar. The amounts of the optional composition components (e.g. buffer, surfactant, peroxidative substance, etc.) are within the skill of a worker in the art.

The chromogenic composition of this invention can be used to determine an analyte which is capable of producing hydrogen peroxide (i.e. an analyte which can participate in a reaction or series of reactions which produce hydrogen peroxide) in an aqueous liquid such as a biological fluid (e.g. human and animal whole blood, blood serum, plasma, feces, spinal fluid, urine, etc.). This composition can be used with the appropriate interactive reagent or combination of reagents which produces hydrogen peroxide upon interaction with the analyte during the assay. The interactive reagents can be mixed with the chromogenic composition either prior to or during the assay. Analytes which can be determined in this manner include glucose, triglycerides, uric acid, lipase, cholesterol, galactose, amino acids, creatine kinase, and others known to one skilled in the clinical chemistry art. For example, to determine uric acid, the composition is used with uricase. To determine cholesterol, the composition is used with cholesterol oxidase and cholesterol ester hydrolase. Other interactive compositions can be fashioned for a given analyte by one skilled in the art. The amounts of the reagents suitable for a given assay are known to one skilled in clinical chemistry. In the context of this disclosure, determination means either qualitative (i.e. merely detection), semi-quantitative or quantitative analysis unless otherwise specified.

The composition and method of this invention are adaptable to both solution and dry element assays. In a solution assay, generally the chromogenic composition (optionally containing interactive reagents) is physically contacted and mixed with a liquid test sample in a suitable container (e.g. test tube, petrie dish, beaker, cuvette, etc.). The resulting solution is incubated for a relatively short time, e.g. about 5 minutes, at a suitable temperature (e.g. about 37° C.). The sample is then evaluated by measuring the amount of dye provided upon reaction of the color-forming coupler with color developing compound in the presence of hydrogen peroxide. The amount of dye can then be correlated to the amount of hydrogen peroxide either initially present in the sample, or produced as a result of the presence of an analyte. Such an evaluation can be done visually or with suitable colorimetric detection equipment and procedures.

The color-forming coupler and color developing compound can be provided as part of a diagnostic test kit for either dry or solution assays. For solution assays, the kit components can be supplied as lyophilized reagents in individual packets having predetermined amounts. Alternatively, they can be provided in bottled or otherwise packaged solutions sufficient in size for one or more assays. Other reagents or non-reactive addenda can also be supplied in the kit along with suitable assay utensils or containers for performing the assay, if desired. A dry analytical element (described below) containing one or more reagents necessary for an assay can also be included as part of a diagnostic test kit.

The composition and method of this invention can also be utilized with a dry analytical element which contains an absorbent carrier material, i.e. a thin sheet of a self-supporting absorbent or bibulous material, such as filter paper or strips, which contains the composition of this invention. Preferably, such elements also contain a peroxidative substance. Such elements are known in the art as test strips, diagnostic elements, dip sticks, diagnostic agents and the like.

When employed in dry chemistry elements, the composition of this invention can be incorporated into a suitable absorbent carrier material by imbibition, impregnation, coating or other suitable technique. Useful absorbent materials are insoluble and maintain their structural integrity when exposed to water or physiological fluids such as urine or serum. Useful elements can be prepared from paper, porous particulate structures, porous polymeric films, cellulose, wood, glass fiber, woven and nonwoven fabrics (synthetic and nonsynthetic) and the like. Useful materials and procedures for making such elements are well known in the art as exemplified in U.S. Pat. No. 3,092,465 (issued June 4, 1963 to Adams et al), U.S. Pat. No. 3,802,842 (issued Apr. 9, 1974 to Lange et al), U.S. Pat. No. 3,915,647 (issued Oct. 28, 1975 to Wright), U.S. Pat. No. 3,917,453 (issued Nov. 4, 1975 to Milligan et al), U.S. Pat. No. 3,936,357 (issued Feb. 3, 1976 to Milligan et al), U.S. Pat. No. 4,248,829 (issued Feb. 3, 1981 to Kitajima et al), U.S. Pat. No. 4,255,384 (issued Mar. 10, 1981 Kitajima et al), and U.S. Pat. No. 4,270,920 (issued June 2, 1981 to Kondo et al), and U.S. Pat. No. 4,312,834 (issued Jan. 26, 1982 to Vogel et al), and U.K. Pat. No. 2,052,057 (published Jan. 21, 1981).

Preferably, the dry analytical elements of this invention have at least one porous spreading zone as carrier material. This zone can be a self-supporting (i.e. composed of a material rigid enough to maintain its integrity), but preferably it is carried on a separate supporting substrate (commonly called a support). Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (reflection or transmission spectroscopy). Useful support materials include paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum or urine is to be assayed.

Useful spreading zones can be prepared using fibrous materials, either mixed with a suitable binder material or woven into a fabric, as described in U.S. Pat. No. 4,292,272 (issued Sept. 29, 1981 to Kitajima et al). Alternatively, and preferably, the spreading zone is prepared from polymeric compositions (e.g. blush polymers) or particulate materials, with or without binding adhesives, as described in U.S. Pat. No. 3,992,158 (issued Nov. 16, 1976 to Przybylowicz et al) and U.S. Pat No. 4,258,001 (issued Mar. 24, 1981 to Pierce et al). Other useful spreading zone materials are described in W. German OLS No. 3,150,102 (published July 29, 1982) and Japanese Patent Publication No. 57(1982)-101760 (published June 24, 1982). It is desirable that the spreading zone be isotropically porous, meaning that the porosity is the same in each direction in the zone as created by interconnected spaces or pores between particles, fibers, polymeric strands, etc.

Particularly useful spreading zones are those having a particulate structure formed by organo-polymeric particles and a polymeric adhesive for these particles as described in the Pierce et al patent noted above.

The elements can have more than one zone, e.g. one or more reagent zones, spreading zones, registration zones, mordant zones, radiation-blocking or filter zones, subbing zones, barrier zones, buffer zones, etc. The zones are generally in fluid contact with each other meaning that fluids, interactive reagents and reaction products (e.g. color dyes) can pass between superposed regions of adjacent zones. Stated in another manner, fluid contact refers to the ability to transport components of a fluid between the zones in fluid contact. Preferably, the zones are separately coated layers, although two or more zones can be a single layer, or a zone can contain two or more separate layers. Besides the references noted above, suitable element formats and components are described, for example, in U.S. Pat. No. 4,042,335 (issued Aug. 16, 1977 to Clement), U.S. Pat. No. 4,132,528 (issued Jan. 2, 1979 to Eikenberry et al), and U.S. Pat. No. 4,144,306 issued Mar. 13, 1979 to Figueras).

The chromogenic composition of this invention can be incorporated in any of the zones of the elements that would be suitable for the particular analysis. The location of other reagents or addenda can be any suitable zone as is known by a worker skilled in the clinical chemistry art.

In the elements of this invention, the amounts of the color-forming coupler and other reagents can be varied widely depending upon the analyte to be determined. Generally, the color-forming coupler is present in a coverage of up to about 3, and preferably from about 0.2 to about 1 $g/m^2$. The peroxidative substance can be present in a coverage within the skill of a worker in the art. For peroxidase, for example, the coverage is generally up to about 150,000, and preferably from about 40,000 to about 60,000 I.U./$m^2$. The oxidizable color developing compound is generally present in a coverage of up to about 2, and preferably from about 0.2 to about 1 $g/m^2$. A variety of other desirable, but optional reagents and addenda can be present in the element in amounts known to one skilled in the art. Such materials include surfactants, buffers, binders, pigments, activators, interactive reagents, etc. In the context of this application, I.U. represents the International Unit for enzyme activity required to catalyze the conversion of 1 $\mu$mole of substrate per minute under standard pH and temperature conditions for the given enzyme.

One embodiment of this invention is a multilayer dry analytical element for determining an analyte. This element comprises a support having thereon, in order and in fluid contact, a hydrophilic registration layer containing a hydrophilic binder material (natural or synthetic), such as gelatin or polyacrylamide, and a spreading/reagent layer containing: (1) an interactive reagent(s) which produces hydrogen peroxide upon interaction with the analyte, (2) a substance having peroxidative activity, and (3) the chromogenic composition as described above. This element can also have a radiation-blocking layer between the registration and spreading/reagent layers. This layer generally contains a reflective pigment (e.g. titanium dioxide or barium sulfate) in a suitable hydrophilic binder (e.g. gelatin).

In a preferred embodiment of this invention, the element spreading/reagent zone comprises glucose oxidase which interacts with the analyte glucose, a peroxidative substance (e.g. peroxidase), an oxidizable color developing compound (e.g. 4-aminoantipyrine), a suitable buffer which maintains the pH in the range of from about 4 to about 7 during the assay (i.e. when spotted with a 1-20 $\mu$l whole blood sample), and a color-forming coupler as described herein.

The coverage of the reagents in the glucose-determining element described above is well within the skill of the worker in the art. For example, glucose oxidase is generally present in a coverage of up to about 80,000, and preferably from about 40,000 to about 60,000, I.U./$m^2$. The peroxidative substance (e.g. peroxidase) is generally present in a coverage of up to about 80,000, and preferably from about 40,000 to about 60,000, I.U./$m^2$. The aminoantipyrine oxidizable compound is generally present in a coverage of up to about 2, and preferably from about 0.2 to about 1 g/mz. The color-forming coupler is generally present in a coverage of up to about 3, and preferably from about 0.2 to about 1 $g/m^2$.

In another embodiment of this invention, a cholesterol assay utilizes a spreading/reagent zone containing cholesterol oxidase, a nonionic surfactant or a protease, cholesterol ester hydrolase, a peroxidative substance (e.g. peroxidase), an oxidizable color developing compound (e.g. 4-aminoantipyrine), a suitable buffer which maintains the pH in the range of from about 4 to about 7 during the assay, and a suitable color-forming coupler as described herein.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, hydrogen peroxide or other analyte determination is made by taking the element from a supply roll, chip packet or other source and physically contacting it with a sample (e.g. 1–20 μl) of the liquid to be tested. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result.

Determination of hydrogen peroxide or other analyte is achieved when the oxidized color developing compound reacts with the color-forming coupler to provide a detectable color dye. This dye can be detected with the unaided eye or with suitable spectrophotometric means and procedures.

In the preparations and examples which follow, the materials were obtained from the following sources: Zonyl FSN TM surfactant from DuPont (Wilmington, Del.), rutile titanium dioxide from Gulf & Western Industries, Inc. (Southfield, Mich.), Daxad TM 30 surfactant from W. R. Grace & Co. (Baltimore, Md.), glucose oxidase from Sigma Chemical (St. Louis, Mo.), peroxidase from Miles Laboratories (Elkhart, Ind.), Kelzan TM thickener from Kelco (Clark, N.J.), and the remainder either prepared using conventional procedures or obtained from Eastman Organic Chemicals (Rochester, N.Y.).

Preparation A: Preparation of N-Sulfopropyltetrahydroquinoline

In a round bottom flask fitted with a stirrer and reflux condenser were placed 50.0 g of tetrahydroquinoline, 48.8 g of 1,3-propanesultone and 500 ml of reagent grade acetonitrile solvent. The mixture was heated at reflux under a nitrogen blanket overnight. The reaction mixture was cooled to ice-bath temperature and the resulting white solid precipitate filtered and washed with cold acetonitrile. A yield of 58 g (60%) of crude product was obtained with a melting point over 200°. Nuclear magnetic resonance (NMR) and mass spectrometry analyses showed the product to be consistent with the assigned structure.

Preparation B: Preparation of 3-(N-2,3-dihydroindolyl)propane sulfonic acid

A mixture of dihydroindole (4.76 g, 40 mmole) and 1,3-propane sultone (4.88 g, 40 mmole) in 50 ml reagent grade acetonitrile was heated under a nitrogen atmosphere and refluxed overnight. After cooling to room temperature, then to ice bath temperature, the resulting white solid was filtered and washed with cold acetonitrile. The yield was 8.1 g (84%), and the product had a melting point of greater then 200° C. Nuclear magnetic resonance (NMR) and elemental analysis showed the product to be consistent with the assigned structure. NMR ($D_2O$): 7.45 (s, 4H), 2.8–4.0 (m, 8H), 2.2 (t, 2H).

The following examples are provided to illustrate the practice of this invention.

EXAMPLE 1

Preparation of 2-N-Quinolylethyl Phosphonic Acid

A mixture of 2.5 g (8.3 mmole) of diethyl 2-N-quinolylethylphosphonate and 10 ml of concentrated HCl was refluxed for 20 hours. The solution was then cooled and concentrated under vacuum. The residue was dissolved in $CH_3CN$ and the solvent removed, yielding 2.5 g of white solid. Nuclear magnetic resonance (NMR) and mass spectral analysis showed the solid to have the assigned structure. $^1$H NMR ($D_2O$): 2.0 (m, 4H), 2.7 (t, 2H), 3.5 (m, 4H), 7.25 (s, 4H). The molecular weight is 241.

EXAMPLE 2

Preparation of Diethyl 2-N-Quinolylethylphosphonate

Tetrahydroquinoline (5.3 g, 40 mmole) and bromoethyldiethyl phosphonate (10.8 g, 44 mmole) were combined in 100 ml reagent acetonitrile. A catalytic amount (~10%) of sodium iodide was added, and the solution was refluxed under nitrogen for 48 hours. The reaction mixture was then cooled to room temperature and the solvent removed under vacuum. Excess phosphonate starting material was removed by distillation. The resulting crude product (5 g) was determined to have the assigned structure by NMR analysis. $^1$H NMR ($CDCl_3$): 1.25 (t, 6H), 2.0 (m, 4H), 2.65 (t, 2H), 3.2 (t, 2H), 3.55 (m, 2H), 4.1 (m, 4H), 6.6 (m, 2H), 6.9 (m, 2H). The compound's molecular weight is 297.

EXAMPLE 3

Dry Analytical Element Useful for Assay of Glucose

Whole blood samples were assayed for glucose in the following manner using the dry analytical element illustrated below.

| | | Dry Coverage Range |
|---|---|---|
| Spreading/ Reagent Layer | Poly(vinyltoluene-co-p-t-butyl-styrene-co-methacrylic acid) (61:37:2 weight ratio) beads | 100–200 g/m$^2$ |
| | Poly(n-butyl acrylate-co-styrene-co-2-acrylamido-2-methylpropane sulfonic acid, sodium salt (70:20:10 weight ratio) | 2–8 g/m$^2$ |
| | Kelzan TM | 0.05–0.3 g/m$^2$ |
| | Zonyl FSN TM surfactant | 0.5–3 g/m$^2$ |
| | N—Sulfopropyltetrahydroquinoline | 0.2–3 g/m$^2$ |
| | 4-Aminoantipyrine.HCl | 0.2–2 g/m$^2$ |
| | 5,5-Dimethyl-1,3-cyclohexanedione | 0.05–5 g/m$^2$ |
| | 6-Amino-4,5-dihydroxy-2-methylpyrimidine | 0.005–0.05 g/m$^2$ |
| | 3,3-Dimethylglutaric acid buffer (pH = 5) | 1–6 g/m$^2$ |
| | Glucose oxidase | 10,000–80,000 I.U./m$^2$ |
| | Peroxidase | 10,000–80,000 I.U./m$^2$ |
| Radiation- | Gelatin (hardened) | 0.5–2 g/m$^2$ |

-continued

| | | Dry Coverage Range |
|---|---|---|
| Blocking Layer | Titanium dioxide (rutile) | 5-20 g/m² |
| | Daxad ™ 30 surfactant | 0.02-0.2 g/m² |
| | Zonyl FSN ™ surfactant | 0.02-0.2 g/m² |
| Registration Layer | Gelatin (hardened) | 2-20 g/m² |
| | Zonyl FSN ™ surfactant | 0.05-0.3 g/m² |
| | Poly(ethylene terephthalate) Support | |

Differing amounts of glucose (58–516 mg/dl) were added to separate samples of human whole blood. A 10 μl aliquot of each sample was spotted on a sample of the analytical element described above. After three minutes at room temperature, the reflection density was recorded at 580 nm with a conventional spectrophotometer. Each whole blood sample was similarly tested three times. The average reflection density is listed in Table I below.

TABLE I

| Sample Glucose Concentration (mg/dl) | Average Reflection Density |
|---|---|
| 58 | 0.40 |
| 118 | 0.63 |
| 234 | 0.99 |
| 332 | 1.20 |
| 422 | 1.27 |
| 516 | 1.33 |

EXAMPLE 4–6

Assays of Glucose Using Various Color-Forming Couplers

Dry analytical elements like that described in Example 3 were prepared containing N-sulfopropyldihydroindole (Example 4), ethyl-2-N-quinolylethyl phosphonate (Example 5) and 2-N-quinolylethyl phosphonic acid (Example 6) as color-forming couplers in place of N-sulfopropyltetrahydroquinoline. Samples of human whole blood containing differing amounts of glucose were assayed with samples of each element by spotting a 10 μl aliquot of each sample on the spreading/ reagent layer of the element. After three minutes at room temperature, the reflection density ($D_R$) was recorded at 585 nm with a conventional spectrophotometer. Each whole blood sample was similarly tested three times. The average reflection densities at the respective glucose concentrations are listed in Tables II and III below.

TABLE II

| Glucose Concentration (mg/dl) | Example 4 - Average $D_R$ at 585 nm |
|---|---|
| 55 | 0.48 |
| 96 | 0.69 |
| 188 | 1.02 |
| 297 | 1.23 |
| 405 | 1.27 |
| 502 | 1.30 |

TABLE III

| | Average $D_R$ at 585 nm | |
|---|---|---|
| Glucose Concentration (mg/dl) | Example 5 | Example 6 |
| 48 | 0.47 | 0.45 |
| 118 | 0.85 | 0.81 |
| 200 | 1.15 | 1.09 |
| 305 | 1.34 | 1.27 |

TABLE III-continued

| | Average $D_R$ at 585 nm | |
|---|---|---|
| Glucose Concentration (mg/dl) | Example 5 | Example 6 |
| 400 | 1.40 | 1.31 |

EXAMPLE 7–8

Comparative Assays for Glucose

These examples compare assays of the present invention utilizing dry analytical elements containing quinoline color-forming couplers to assays (Controls A and B) utilizing aniline color-forming couplers. Example 7 compared N-sulfopropyltetrahydroquinoline to N-ethyl-N-2-sulfoethyl toluidine (Control A). Example 8 compared N-2-hydroxyethyltetrahydroquinoline to N-methyl-N-2-hydroxyethylaniline (Control B).

The dry analytical elements used in these comparisons had the format and composition of the element described in Example 3 except for the difference in color-forming coupler. Samples of human whole blood containing differing amounts of glucose were assayed with samples of each element (Examples and Controls) by spotting a 10 μl aliquot of each sample on the spreading/reagent layer of the element. After three minutes at room temperature, the reflection density ($D_R$) was recorded at 585 nm with a conventional spectrophotometer. Each whole blood sample was similarly tested three times. The average reflection densities at the respective glucose concentrations are listed in Tables IV and V below. The elements of this invention consistently showed improved sensitivity (as indicated by greater ($D_R$)) over the respective Controls over the range of glucose concentrations tested.

TABLE IV

| | Average $D_R$ at 585 nm | |
|---|---|---|
| Glucose Concentration (mg/dl) | Example 7 | Control A |
| 55 | 0.58 | 0.53 |
| 96 | 0.84 | 0.77 |
| 188 | 1.28 | 1.18 |
| 297 | 1.55 | 1.42 |
| 405 | 1.61 | 1.48 |
| 502 | 1.63 | 1.48 |

TABLE V

| | Average $D_R$ at 585 nm | |
|---|---|---|
| Glucose Concentration (mg/dl) | Example 8 | Control B |
| 73 | 0.58 | 0.56 |
| 108 | 0.77 | 0.70 |
| 199 | 1.16 | 1.08 |
| 298 | 1.36 | 1.33 |
| 398 | 1.44 | 1.36 |
| 502 | 1.45 | 1.38 |

EXAMPLE 9

Comparative Assay to Uric Acid

This example compares the use of a quinoline color-forming coupler to the use of a toluidine color-forming coupler in a solution uric acid assay. Uric acid is an analyte which is commonly present in low concentrations in human sera.

An enzyme solution was prepared by diluting 40 mg of uricase (0.3 I.U./mg) and 3 mg of peroxidase (1237 I.U./mg) to 8 ml with 0.01 molar borate buffer (pH 8.7).

Two chromogenic compositions comprising 45 mg of 4-aminoantipyrine and either 42.9 mg of N-ethyl-N-2-sulfoethyl toluidine (Control) or 41.3 mg of N-sulfopropyltetrahydroquinoline (Example 9), respectively, were prepared. Each composition was diluted to 10 ml with 0.01 molar borate buffer (pH 8.7).

A stock uric acid solution was prepared with 1.6 mg uric acid in 10 ml of dilute potassium carbonate.

The assay was carried out by mixing 0.1 ml of each chromogenic composition with 0.1 ml of the enzyme solution and various amounts of the uric acid stock solution (shown in Table IV below) to form assay solutions. Borate buffer was added to each assay solution which had a volume less than 0.3 ml in order to bring the volume up to that level.

The reagents in each assay solution were allowed to react for about 10 minutes, after which 3 ml of borate was added. The optical density of each assay solution was measured, at 555 nm for Example 9 and at 553 nm for the Control. The results are provided in Table IV below. The data reflect the subtraction of optical densities of blank assay solutions (i.e. no uric acid present). It can be seen from the data that the composition of the present invention provides consistently significantly greater optical density over the Control composition. This improvement can be particularly advantageous in the determination of very low concentrations (e.g. less than about 0.3 millimolar) of hydrogen peroxide or of analyte which can react to produce hydrogen peroxide.

TABLE IV

| Uric Acid Concentration (millimolar) | Optical Density Control Assay | Optical Density Example 9 Assay | % Improvement (Example 9 - Control) |
|---|---|---|---|
| 0.03 | 0.032 | 0.040 | 22.5 |
| 0.07 | 0.063 | 0.079 | 21.5 |
| 0.16 | 0.109 | 0.150 | 28 |
| 0.3 | 0.214 | 0.264 | 20 |

The invention has been described in detail with particular reference to preferred embodiments thereof, but it will be understood that variations and modifications can be effected within the spirit and scope of the invention.

We claim:

1. A chromogenic composition for the determination of hydrogen peroxide in an aqueous liquid, said composition comprising:
   (1) a color-forming coupler of the structure:

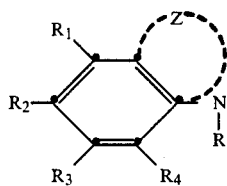

wherein
   R is a water solubilizing group,
   $R_1$, $R_2$, $R_3$ and $R_4$ are independently hydrogen, alkyl, alkoxy, aryl, aryloxy, a heterocyclic group, halo, amino or R, and
   Z represents the carbon atoms necessary to complete the nucleus of a N-substituted 5- or 6-membered fused ring, and
   (2) an oxidizable color developing compound which is capable of reacting with said coupler in the presence of both hydrogen peroxide and a substance having peroxidative activity to produce a color dye.

2. The composition of claim 1 wherein said oxidizable color developing compound is 4-aminoantipyrine.

3. The composition of claim 1 wherein R is alkyl, cycloalkyl or aryl, each substituted with one or more sulfo, hydroxy, carboxy, phosphono, quaternary amino, sulfonium or phosphonium groups or equivalent esters or salts.

4. The composition of claim 3 wherein R is alkyl substituted with one or more sulfo, hydroxy, carboxy, phosphono moieties or equivalent esters or salts, $R_1$, $R_2$, $R_3$ and $R_4$ are independently hydrogen, alkyl of 1 to 3 carbon atoms, alkoxy of 1 to 3 carbon atoms or halo, and Z represents the carbon atoms necessary to complete the nucleus of a N-substituted 6-membered fused ring.

5. The composition of claim 4 wherein R is $$-CH_2)_mSO_3M \text{ or } -CH_2)_mPO(OR_5)(OR_6)$$

wherein m is 1 to 5, M is a cation, $R_5$ and $R_6$ are independently hydrogen or alkyl of 1 to 5 carbon atoms, and said fused ring is saturated.

6. The composition of claim 1 further comprising an interactive reagent(s) which produces hydrogen peroxide upon interaction with an analyte.

7. The composition of claim 1 further comprising a substance having peroxidative activity.

8. A dry analytical element for the determination of hydrogen peroxide or of an analyte which can react to produce hydrogen peroxide in an aqueous liquid, said element comprising an absorbent carrier material containing the chromogenic composition of claim 1.

9. A dry analytical element for the determination of an analyte in an aqueous liquid, said element comprising a support having thereon one or more zones one of which comprising a porous spreading zone, and containing in any of said zones:
   (1) an interactive reagent(s) which produces hydrogen peroxide upon interaction with an analyte,
   (2) a color forming coupler of the structure:

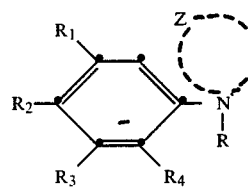

wherein
R is a water solubilizing group,
$R_1$, $R_2$, $R_3$ and $R_4$ are independently hydrogen, alkyl, alkoxy, aryl, aryloxy, a heterocyclic group, halo, amino or R, and
Z represents the carbon atoms necessary to complete the nucleus of a N-substituted 5- or 6-membered fused ring, and
(3) an oxidizable color developing compound which is capable of reacting with said coupler in the presence of both hydrogen peroxide and a substance having peroxidative activity to produce a color dye.

10. The element of claim 9 further comprising a substance having peroxidative activity.

11. The element of claim 9 wherein R is alkyl substituted with one or more sulfo, hydroxy, carboxy, phosphono moieties or equivalent esters or salts, R1, R2, R3, and R4 are independently hydrogen, alkyl of 1 to 3 carbon atoms, alkoxy of 1 to 3 carbon atoms or halo, and Z represents the carbon atoms necessary to complete the nucleus of a N-substitued 6 membered fused ring.

12. The element of claim 11 wherein R is $$-CH_2)_mSO_3M \text{ or } -CH_2)_mPO(OR_5)(OR_6)$$

wherein m is 1 to 5, M is a cation, and R5 and R6 are independently hydrogen or alkyl of 1 to 5 carbon atoms, and said fused ring is saturated.

13. The element of claim 9 wherein said interactive reagent is uricase.

14. A dry analytical element for the determination of glucose in an aqueous liquid, said element comprising a support having thereon, in order and in fluid contact, a registration layer and a porous spreading/reagent layer, said element containing in any of said layers:
(1) glucose oxidase,
(2) peroxidase,
(3) a color-forming coupler of the structure:

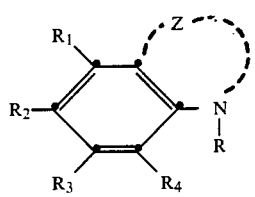

wherein
R is a water solubilizing group,
R1, R2, R3 and R4 are independently hydrogen, alkyl, alkoxy, aryl, aryloxy, a heterocyclic group halo, amino or R, and
Z represents the carbon atoms necessary to complete the nucleus of a N-substituted 5- or 6-membered fused ring, and
(4) an oxidizable color developing compound which is capable of reacting with said coupler in the presence of both hydrogen peroxide and peroxidase to produce a color dye.

15. The element of claim 14 further comprising a radiation-barrier layer between said registration and spreading/reagent layers.

16. The element of claim 14 wherein said oxidizable color developing compound is 4-aminoantipyrine, and said color-forming coupler is

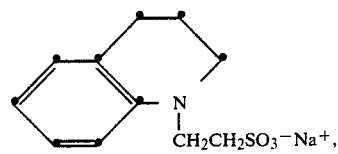

-continued

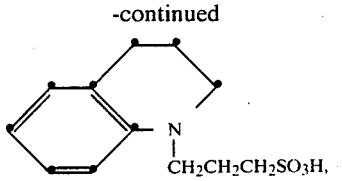

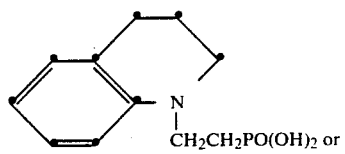

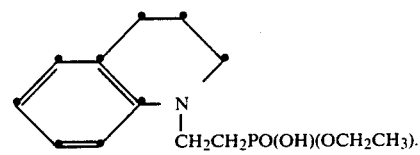

17. A method for determining hydrogen peroxide or an analyte which reacts to produce hydrogen peroxide in an aqueous liquid, said method comprising the steps of:
A. in the presence of a substance having peroxidative activity, physically contacting a sample of a liquid with a colorimetric composition comprising a color-forming coupler of the structure:

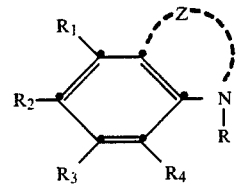

wherein
R is a water solubilizing group,
r1, R2, R3 and R4 are independently hydrogen, alkyl, alkoxy, aryl, aryloxy, a heterocyclic group, halo, amino or R, and
Z represents the carbon atoms necessary to complete the nucleus of a N-substituted 5- or 6-membered fused ring, and
an oxidizable color developing compound which is capable of reacting with said coupler in the presence of both hydrogen peroxide and said peroxidative substance
to produce a color dye, and
B. detecting said dye as a result of the presence of hydrogen peroxide or an analyte which reacts to produce hydrogen peroxide.

18. The method of claim 17 wherein said analyte is glucose and said contacting step A occurs in the presence of glucose oxidase.

19. A diagnostic test kit for the determination of hydrogen peroxide, said kit comprising a container means containing:
(1) a color-forming coupler of the structure:

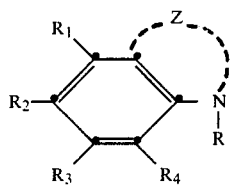

wherein

R is a water solubilizing group, $R_1$, $R_2$, $R_3$ and $R_4$ are independently hydrogen, alkyl, alkoxy, aryl, aryloxy, a heterocyclic group, halo, amino or R, and Z represents the carbon atoms necessary to complete the nucleus of a N-substituted 5- or 6-membered fused ring, and (2) an oxidizable color developing compound which is capable of reacting with said coupled in the presence of both hydrogen peroxide and a substance having peroxidative activity to produce a color dye.

20. A color-forming coupling compound of the structure:

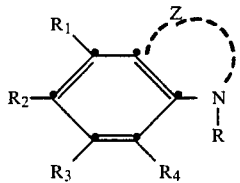

wherein

R is a water solubilizing group having one or more phosphono groups or equivalent esters or salts.

$R_1$, $R_2$, $R_3$ and $R_4$ are independently hydrogen, alkyl, alkoxy, aryl, aryloxy, a heterocyclic group, halo, amino or R, and Z represents the carbon atoms necessary to complete the nucleus of a N-substituted 5- or 6-membered fused ring.

21. The compound of claim 20 wherein R is
—$CH_2)_m PO(OR_5)(OR_6)$ wherein m is 1 to 5 and $R_5$ and $R_6$ are independently hydrogen or alkyl of 1 to 5 carbon atoms, and $R_1$, $R_2$, $R_3$ and $R_4$ are independently hydrogen, alkyl of 1 to 3 carbon atoms, alkoxy of 1 to 3 carbon atoms or halo.

22. The compound of claim 20 wherein Z represents the carbon atoms necessary to complete the nucleus of a saturated N-substituted 6-membered fused ring.

23. The compound of claim 22 selected from the group consisting of:

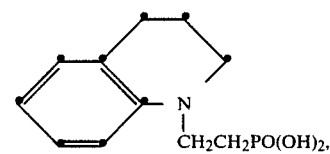

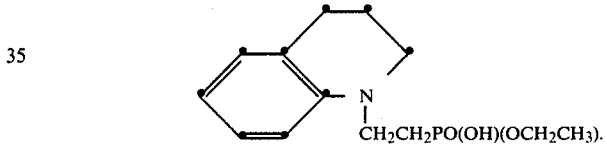

* * * * *